United States Patent
Sloman

(10) Patent No.: US 7,548,783 B1
(45) Date of Patent: Jun. 16, 2009

(54) IMPLANTABLE CARDIAC STIMULATION DEVICE HAVING A SYSTEM FOR PROVIDING ATRIAL THERAPY BASED ON CIRCADIAN VARIATIONS AND METHOD

(75) Inventor: Laurence S. Sloman, West Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 557 days.

(21) Appl. No.: 11/330,208

(22) Filed: Jan. 11, 2006

(51) Int. Cl.
  *A61N 1/362* (2006.01)
(52) U.S. Cl. .................................. 607/14; 600/515
(58) Field of Classification Search ............ 607/14, 607/115, 116, 119; 128/905, 923, 922; 600/508, 600/513, 515
  See application file for complete search history.

(56) References Cited

U.S. PATENT DOCUMENTS

| | | | | |
|---|---|---|---|---|
| 4,572,192 A | * | 2/1986 | Jackman et al. ............... | 607/14 |
| 5,733,312 A | | 3/1998 | Schloss et al. ................ | 607/17 |
| 6,058,328 A | * | 5/2000 | Levine et al. .................. | 607/14 |
| 6,161,041 A | | 12/2000 | Stoop et al. ................... | 607/14 |
| 6,711,439 B1 | * | 3/2004 | Bradley et al. ................. | 607/9 |
| 2004/0215253 A1 | * | 10/2004 | Weinberg ...................... | 607/9 |

FOREIGN PATENT DOCUMENTS

EP  1308182 A2 * 5/2003

* cited by examiner

*Primary Examiner*—Mark W Bockelman
*Assistant Examiner*—Elizabeth So

(57) ABSTRACT

An implantable cardiac stimulation device selects an arrhythmia therapy based upon the time of day. The device comprises an arrhythmia detector that detects an accelerated arrhythmia of a heart, and a data circuit that maintains a time record of cardiac cycle lengths developed during detected accelerated arrhythmias. A therapy circuit provides a selected therapy to the heart based upon the maintained time record of cardiac cycle lengths and the time of day.

21 Claims, 2 Drawing Sheets

IMPLANTABLE CARDIAC STIMULATION DEVICE HAVING A SYSTEM FOR PROVIDING ATRIAL THERAPY BASED ON CIRCADIAN VARIATIONS AND METHOD

FIELD OF THE INVENTION

The present invention generally relates to an implantable cardiac stimulation device that provides electrical therapy to a patient's heart. The present invention more particularly relates to such a device that provides atrial tachyarrhythmia therapy to a heart based upon recorded circadian variations in atrial activity.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or evoked responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or evoked responses are sensed between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Implantable cardiac defibrillators (ICD's) are also well known in the art. These devices generally include an arrhythmia detector that detects accelerated arrhythmias, such as tachycardia or fibrillation. When such a tachyarrhythmia is detected, a pulse generator delivers electrical therapy to the patient's heart. A therapy for tachycardia may be anti-tachycardia pacing and a therapy for fibrillation may be a defibrillating shock. Such therapies are well known.

During atrial tachycardia (AT), the atria of the heart beat rapidly at an abnormally high rate. This can cause the ventricles to in turn beat at a high rate. Cardiac output may be reduced. The patient may experience dizziness or feel fatigued. Although not immediately life threatening, it is generally unpleasant to a patient.

Atrial fibrillation (AF) is a common atrial tachyarrhythmia and can occur suddenly. It results in rapid and chaotic activity of the atria of the heart. The chaotic atrial activity in turn causes the ventricular activity to become rapid and variable. Although not life threatening, it is associated with strokes thought to be caused by blood clots forming in areas of stagnant blood flow as a result of prolonged atrial fibrillation. In addition to strokes, symptoms of atrial fibrillation may include fatigue, syncope, congestive heart failure, weakness and dizziness.

Implantable cardiac device therapies are known which assist in precluding the occurrence of atrial tachyarrhythmia episodes. One therapy deals with pacing the atria at a rate slightly faster than the normal intrinsic rate. This is believed to maintain capture of the atria and more organized cardiac behavior, thus preventing an accelerated atrial arrhythmia from occurring. Unfortunately, this atrial pacing at a slightly faster atrial rate than normal can become annoying to a patient.

Antitachycardia pacing of the atria is also known to treat atrial tachycardia (AT) and assist in preventing an acceleration of the atrial rate into fibrillation. Here again the atria are paced at a rate above the normal intrinsic rate. It has been found to be most effective for more organized accelerated atrial rates corresponding to, for example, mean atrial cycle lengths above about 250 mS.

Less organized accelerated atrial rates corresponding to mean atrial cycle lengths less than 250 mS are generally best treated with a low voltage atrial cardioversion shock. When necessary, a higher voltage atrial defibrillation shock may be appropriate.

Obviously, no single therapy is always the appropriate therapy. At times, preventive therapy may be desirable while at other times termination therapy may be appropriate.

Because of the wide range of available accelerated atrial rhythm therapies, it would be helpful to have a way to make an appropriate therapy selection best suited for an individual patient. Recently, it has been observed that accelerated atrial arrhythmias may have a circadian quality. This may be used to advantage in predicting which of the many therapies should be employed at a given time. The present invention addresses this and other issues.

SUMMARY

The invention provides an implantable cardiac stimulation device that selects an arrhythmia therapy based upon the time of day. The device comprises an arrhythmia detector that detects an accelerated arrhythmia of a heart, a data circuit that maintains a record of cardiac cycle lengths during detected accelerated arrhythmias as a function of time of day, and a therapy circuit that provides a selected therapy to the heart based upon the maintained record of cardiac cycle lengths and time of day.

The arrhythmia detector detects an accelerated atrial arrhythmia. The cardiac cycle lengths may be atrial cycle lengths and, more particularly, mean atrial cycle lengths. The data circuit may maintain a plurality of histograms, each histogram having a plurality of time of day bins corresponding to a given atrial cycle length.

The selected therapy may be an accelerated arrhythmia preventive therapy. The selected therapy may be an accelerated arrhythmia termination therapy responsive to detection of an accelerated arrhythmia by the arrhythmia detector.

The invention further provides an implantable cardiac stimulation device comprising an arrhythmia detector that detects an accelerated atrial arrhythmia of a heart and a data circuit that maintains a record of atrial cycle lengths versus time of day occurring during detected accelerated atrial arrhythmias. The device further comprises a therapy circuit that provides a selected therapy to the heart based upon the record of atrial cycle lengths versus time of day.

The invention further provides a method for use in an implantable cardiac stimulation device. The method comprises detecting accelerated arrhythmias of a heart, recording cardiac cycle lengths during episodes of detected accelerated arrhythmias as a function of time of day, and providing a selected therapy to the heart based upon the maintained record of cardiac cycle lengths as a function of time of day.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
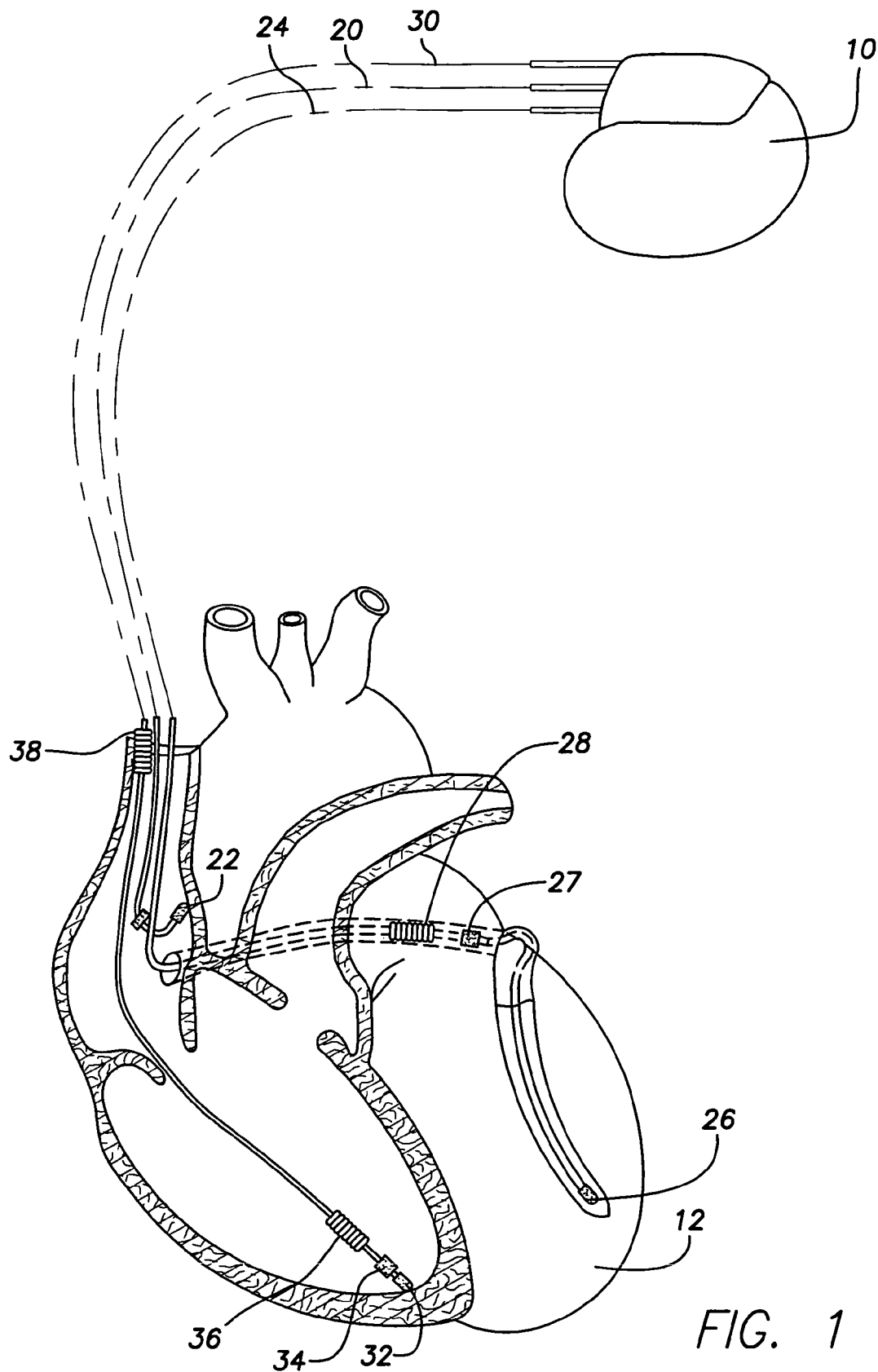
FIG. 1 is a simplified diagram illustrating an implantable stimulation device according to an embodiment of the invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein the phrase "coronary sinus region" refers to the vasculature of the left ventricle, including any portion of the coronary sinus, great cardiac vein, left marginal vein, left posterior ventricular vein, middle cardiac vein, and/ or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
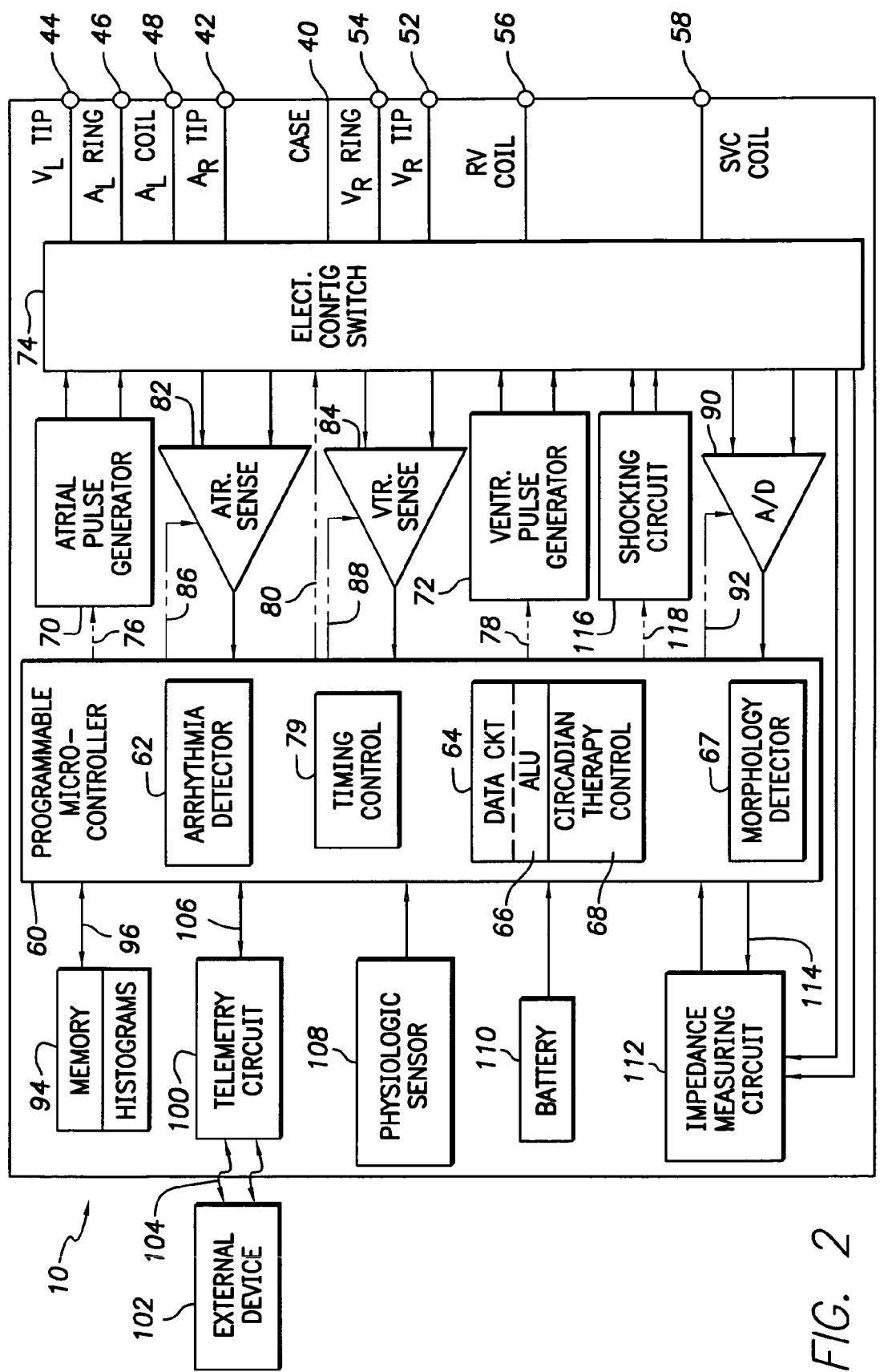
FIG. 2 is a functional block diagram of the implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 includes an arrhythmia detector 62. It utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart. The therapy may be aimed at terminating a detected arrhythmia or preventing an arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With continued reference to FIG. 2, it will be noted that the microcontroller 60 embodies a data circuit 64 and a circadian therapy control circuit 68. The data circuit 64 includes an arithmetic logic unit (ALU) 66.

In accordance with the broader aspects of the invention, the data circuit gathers data during episodes of detected accelerated atrial arrhythmias and keeps a time record of the data. The time record may be analyzed and used by the circadian therapy control 68 to predict, based upon the time of day, when an accelerated atrial arrhythmia therapy is needed and to select the appropriate therapy. The therapy may be therapy to prevent an accelerated atrial arrhythmia or therapy to terminate a detected accelerated atrial arrhythmia.

According to this embodiment, the time record is a time of day record generated by the data circuit. During episodes of detected accelerated atrial arrhythmias, the data circuit determines a mean atrial cycle length (MACL) every thirty (30) seconds, for example. The ALU 66 is employed for calculating the MACLs. To this end, the data acquisition system 90 generates intracardiac electrograms (IEGMs) of atrial activity during AT or AF episodes, digitizes the IEGMs and stores the digital samples in memory 94.

A morphology detector 67 determines the beginning and end of each atrial cycle. The ALU then computes an MACL for each 30 second interval. The MACLs are then stored in histograms within a memory section 95 of memory 94. The histograms may be maintained, for example, for mean atrial cycle lengths between 150 millisecond (mS) and 300 millisecond (mS). A typical MACL resolution sampling interval may be 7.8 mS, for example. Hence, each MACL has an associated histogram and each histogram has, in this example, 24 (hours) times 60 (minutes) times 60 (seconds) divided by 30 (seconds) time of day bins. There is one histogram for each measured MACL. Separate histograms may be provided for MACL measurements greater than 300 mS or less than 150 mS.

During a predetermined sampling time following device implant, the data circuit 64 collects the MACL measurements during detected accelerated atrial arrhythmia episodes. After the sampling time, a three dimensional time history results. The time history includes the MACLs along the X axis, the histogram time of day bins along the Y axis, and the counts (MACL and time of day) along the Z axis. The circadian therapy control may then determine the circadian variation of MACL. Bins that have the highest counts at a particular time of day indicate a circadian peak.

The peak or peaks may be used to tailor antitachycardia pacing (ATP) therapy. As an example, the therapy control 68 can call for more aggressive preventive ATP during those times of day when high MACL is indicated. During those times when a smaller MACL is indicated, indicating more variable and disorganized atrial activity, an automatic mode switch (AMS) to a non-atrial tracking mode may be in order.

When an accelerated arrhythmia is detected, the time of day record may be accessed by the therapy control 68 to determine the best termination therapy. The termination therapy may be one of overdrive pacing, a low energy cardioversion shock, or a higher energy defibrillation shock, depending on the time of day record history. The therapy may even be each of the above, in order, until termination is achieved.

Hence, the variations in the circadian MACLs as may be determined from the histograms may be used to predict when preventive therapy is called for to prevent an episode of an accelerated atrial arrhythmia (AT or AF) from occurring. It may further be used to advantage to titrate or select the stimulation therapy most appropriate when AT or AF is detected. As a result, certain therapies, such as overdrive therapy need not be required on a continuous basis, but only used when necessary. This provides for increased patient comfort and device battery longevity.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   an arrhythmia detector configured to detect an accelerated arrhythmia of a heart;
   a data circuit configured to, during a predetermined sampling period, measure a plurality of cardiac cycle lengths during detected accelerated arrhythmias, determine a time of day corresponding to each of the measured cardiac cycle lengths and generate a record comprising a count of the number of times a given measured cardiac cycle length occurs within a time-of-day period; and
   a therapy circuit configured to, subsequent to the predetermined sampling period and, upon detection of an accelerated arrhythmia, provide a selected therapy to the heart based upon the time of day of accelerated arrhythmia detection and the predetermined count corresponding to the time of day of accelerated arrhythmia detection.

2. The device of claim 1 wherein the arrhythmia detector detects an accelerated atrial arrhythmia.

3. The device of claim 2 wherein the cardiac cycle lengths are atrial cycle lengths.

4. The device of claim 3 wherein the atrial cycle lengths are mean atrial cycle lengths.

5. The device of claim 3 wherein the record comprises a plurality of histograms, each histogram having a plurality of time of day bins corresponding to a given atrial cycle length.

6. The device of claim 1 wherein the selected therapy is an accelerated arrhythmia preventive therapy.

7. The device of claim 1 wherein the selected therapy is an accelerated arrhythmia termination therapy responsive to detection of an accelerated arrhythmia by the arrhythmia detector.

8. An implantable cardiac stimulation device comprising:
    an arrhythmia detector configured to detect an accelerated arrhythmia of a heart;
    a data circuit configured to, during a predetermined sampling period, measure a plurality of atrial cycle lengths occurring during detected accelerated atrial arrhythmias, determine a time of day corresponding to each of the measured atrial cycle lengths, and generate a record comprising a count of the number of times a given measured atrial cycle length occurs within a time-of-day period; and
    a therapy circuit configured to, subsequent to the predetermined sampling period and, upon detection of an accelerated atrial arrhythmia, provide a selected therapy to the heart based upon the time of day of accelerated atrial arrhythmia detection and the predetermined count corresponding to the time of day of accelerated atrial arrhythmia detection.

9. The device of claim 8 wherein the atrial cycle lengths are mean atrial cycle lengths.

10. The device of claim 9 wherein the data circuit records the mean atrial cycle lengths periodically during detected accelerated atrial arrhythmias.

11. The device of claim 10 wherein the data circuit records the mean atrial cycle length every thirty seconds.

12. The device of claim 8 wherein the record comprises a plurality of histograms, each histogram having a plurality of time of day bins corresponding to a given atrial cycle length.

13. The device of claim 12 wherein the data circuit maintains a histogram for each one of a plurality of atrial cycle lengths between 150 mS and 300 mS.

14. The device of claim 8 wherein the selected therapy is an accelerated atrial arrhythmia preventive therapy.

15. The device of claim 8 wherein the selected therapy is an accelerated atrial arrhythmia termination therapy responsive to detection of an accelerated atrial arrhythmia by the arrhythmia detector.

16. In an implantable cardiac stimulation device, a method comprising:
    detecting accelerated arrhythmias of a heart;
    during a predetermined sampling period, measuring a plurality of cardiac cycle lengths during episodes of detected accelerated arrhythmias, determining a time of day corresponding to each of the measured cardiac cycle lengths, and generating a record comprising a count of the number of times a given measured cardiac cycle length occurs within a time-of-day period; and
    subsequent to the predetermined sampling period and, upon detection of an accelerated arrhythmia, providing a selected therapy to the heart based upon the time of day of accelerated arrhythmia detection and the predetermined count corresponding to the time of day of accelerated arrhythmia detection.

17. The method of claim 16 wherein the detecting step includes detecting accelerated atrial arrhythmia.

18. The method of claim 16 wherein the cardiac cycle lengths are atrial cycle lengths.

19. The method of claim 18 wherein the atrial cycle lengths are mean atrial cycle lengths.

20. The method of claim 18 wherein the record comprises a plurality of histograms, each histogram having a plurality of time of day bins corresponding to a given atrial cycle length.

21. The device of claim 1 wherein the selected therapy is more aggressive for higher counts and less aggressive for lower counts.

\* \* \* \* \*